(12) United States Patent
Schulman et al.

(10) Patent No.: US 9,480,410 B1
(45) Date of Patent: Nov. 1, 2016

(54) METHOD FOR PROVIDING STIFFNESS ENHANCED FILAMENTS

(71) Applicant: ALFRED E. MANN FOUNDATION FOR SCIENTIFIC RESEARCH, Santa Clarita, CA (US)

(72) Inventors: Joseph H. Schulman, Santa Clarita, CA (US); David L. Hankin, Beverly Hills, CA (US)

( * ) Notice: Subject to any disclaimer, the term of this patent is extended or adjusted under 35 U.S.C. 154(b) by 614 days.

(21) Appl. No.: 13/863,271

(22) Filed: Apr. 15, 2013

Related U.S. Application Data

(62) Division of application No. 12/819,698, filed on Jun. 21, 2010, now Pat. No. 8,442,614.

(51) Int. Cl.
*A61B 5/04* (2006.01)
*A61N 1/05* (2006.01)

(52) U.S. Cl.
CPC ......... *A61B 5/04001* (2013.01); *A61N 1/0526* (2013.01); *A61N 1/0551* (2013.01)

(58) Field of Classification Search
CPC ........... A61B 5/04001; A61N 1/0529; A61N 1/0551
USPC ....... 264/279.1, 279, 277, 640, 641
See application file for complete search history.

(56) References Cited

U.S. PATENT DOCUMENTS

| 3,140,325 A * | 7/1964 | Graff ................. B29C 51/10 156/224 |
| 2005/0113658 A1 * | 5/2005 | Jacobson .......... A61B 5/14532 600/342 |

* cited by examiner

*Primary Examiner* — Stella Yi
(74) *Attorney, Agent, or Firm* — Lewis Roca Rothgerber Christie LLP

(57) ABSTRACT

Methods for making biocompatible stiffness enhanced pliable electrically conductive filaments configured for contact with living tissue and electrical communication with such tissue. The pliability of a filament allows the distal end of the filament to remain at the original site of penetration into the tissue despite the movement of the tissue relative to its surrounding environment. To temporarily stiffen the filament, a soluble stiffness enhancing coating is disposed over the filament. The coating may be in the form of a liquid which dries to a solid state after being applied to the filament and renders the filament sufficiently rigid such that under appropriate force, the filament is capable of penetrating into dense tissue. Once in place the stiffness enhancing coating dissolves due to contact with body fluids, the filament, in the absence of such coating, returns to its initial pliability.

20 Claims, 9 Drawing Sheets

METHOD FOR PROVIDING STIFFNESS ENHANCED FILAMENTS

FIELD OF THE INVENTION

The present invention relates to a stiffness enhanced pliable filament configured for penetration into and contact with living tissue and capable of electrical communication with the tissue. More particularly, the present invention provides at least one or an array of similar electrodes, each electrode having a durable, hard, yet dissolvable stiffness enhancing coating or encasement, to facilitate initial penetration into the tissue and then electrical contact with the tissue once the coating/encasement dissolves.

BACKGROUND OF THE INVENTION

For at least a decade scientists have attempted to attach electrodes or arrays of electrodes to tissue in order to monitor individual neurons in either the brain or nerves in order to electrically stimulate or sense neuron activity to treat nerve damaged maladies. What has been lacking is a relatively simple and rapid yet effective method of attaching an array of electrodes to tissue for monitoring neuron activity where the electrodes will remain reliably connected and functioning for an extended period of time to an active patient.

One major problem facing scientists in this endeavor is the fact that tissue such as the brain and nerves, has protective coverings that must be penetrated by the array of electrodes in order to accomplish the stimulating and monitoring function related to neurons at a desired site in the tissue. In order to accomplish successful penetration, the electrodes are mounted to a supporting platform and preferably have stiff and sharply pointed distal tips. For proper penetration it is considered necessary to impart sufficient impact on the supporting platform to cause an insertion speed of no less than 8.3 meters/second. Even with such insertion speeds, it will be recognized that without any anchoring mechanism, there will most likely be a disconnection between the electrode tips and the tissue during significant movement of the patient.

What is needed therefore, when considering long term stability, is an electrode that maintains electrical connection with the site selected for neuron monitoring and stimulation despite severe movements by the patient, thus being mechanically isolated from the platform while being in electrical communication with the platform.

The filament of an embodiment of the present invention is formed of a biocompatible stiffness enhanced pliable electrically conductive material which accommodates both the application of tissue stimulating electrical signals as well as the sensing of electrical signals emanating from the tissue. A contemplated application of the filament is in the field of neural prosthesis for the restoration of sensory and motor function and in particular in the design of a brain machine interface for neuroprosthetic control. The implications, practical engineering challenges and short comings of such machine interface design have been well documented over the recent past.

For example, U.S. Patent Application Publication No. 2007/0067007 published Mar. 22, 2007, and assigned to the same assignee hereof and incorporated by reference herein in its entirety discloses a new and novel hermetically sealed three dimensional electrode array contemplated for use in applications for neuron interface especially involving human nerves and the brain. The publication is also rich in identifying multiple references relating to the field of neural prosthesis.

As will be appreciated, the design and fabrication of the elements used to establish electrical contact with living tissue has been a daunting task. Electrode designs of the past have resulted in electrode arrays that have been rigid and typically of relatively large diameter. On the advantage side, such electrodes provide for reliable penetration and therefore contact with selected living tissue. On the disadvantage side the electrodes are not capable of individual movement in concert with moving tissue with which the electrodes are in contact. This is particularly important when considering permanently stiff and rigid electrodes used for implant in the human brain to detect sensory cortex signals and provide motor cortex stimulation signals.

Access to the motor and sensory cortex portions of the brain for neuron contact, especially with the use of miniaturized battery powered micro stimulators/sensors as described in U.S. Pat. No. 6,185,452, is particularly advantageous in accomplishing functional electrical stimulation in patients having interruptions in neuromuscular pathways, leading to severely physically compromised and handicapped patients.

As is widely understood, the brain is protected by the thick bones of the skull and is suspended in cerebrospinal fluid and as such is capable of relative movement in the fluid. It is estimated that the brain contains 50-100 billion neurons of which about 10 billion are cortical pyramidal cells which pass signals to each other via approximately 100 trillion synaptic connections. The signals are very site specific such that a signal from the sensory cortex relating for example, to the eyelid, will emanate from a particular site whether or not that site has experienced relative movement due to movement of the brain in the fluid. Movement of the brain may occur for example, when the patient jumps or runs or falls or moves his head in a rapid manner and the like.

Movement of adjacent portions of brain tissue also create significant problems in that although one electrode in an electrode array may consistently monitor signals from a pre-determined site, an adjacent electrode may lose consistency by monitoring other albeit adjacent tissue signals than from the intended site. Tissue deformation and injury is another potential problem, in that the rigidity of the electrodes which is required during implant to penetrate living tissue, functions as a rigid blade as the tissue moves below it potentially inflicting injury to the tissue.

Contemporary philosophy on the nature of the electrodes is described in a textbook entitled Neural Prosthesis for Restoration of Sensory and Motor Function, edited by John K. Chapin and Karen A. Moxon, published by CRC Press, ISBN 0-8493-2225-1.

As described in the referenced textbook, wires intended for neuroprosthetic devices to record from or stimulate the neural tissue, must have a small diameter while maintaining adequate stiffness and tip shape to penetrate the dura and traverse the tissue with minimal bending and mechanical disturbance to adjacent tissue. Benefits were enumerated in the use of 25-50 micron wires including being strong enough to go through the dura of certain animals and rigid enough to be lowered into the correct position. Deficiencies were also enumerated in the use of uncoated wire smaller than 25 microns in that penetrating the dura was difficult and it can be diverted by a fiber bundle when lowered into the brain and therefore, they often do not end up in the intended brain site. Thus electrodes formed of wire filaments in the range of about 10 microns to 25 microns would undoubtedly be beyond the scope of the prior art.

In order to provide an electrode not shown or suggested in the prior art, the electrode and in particular, the distal tip of the electrode which is in electrical contact with the tissue, must at one time be stiff and sufficiently rigid to accommodate penetration of the electrode into the dura and then the brain tissue, but then become or return to sufficient pliability and flexibility to move in concert with the moving tissue into which the electrode has penetrated without any movement away from the original site of penetration of the distal tip in the brain tissue. The filament of the present invention provides the above characteristics.

SUMMARY OF THE INVENTION

An embodiment of the invention includes a dual state biocompatible electrically conductive filament configured for electrical contact with living tissue. The filament has an initial uncoated first state wherein the filament is very pliable and flexible and provides for repeated bending without breaking. In a coated second state, the filament is coated with a dissolvable stiffness enhancing material that provides stiffness and rigidity to the filament making it difficult to bend so as to permit the filament to accurately and reliably penetrate into tissue and thus be positioned at a desired site in the tissue. Once the filament is positioned in place, the coating material dissolves under the action of body fluids or other provided fluids and the filament loses its rigidity and returns to its initial pliable state. Although the filament is described in terms of being configured for contact with living tissue, applications requiring a filament with a stiff or rigid state to accommodate penetration into penetrable matter which filament then returns to a pliable or flexible state some time after being positioned in place and in contact with fluids, is within the contemplation of the invention.

A further embodiment of the invention includes at least one or an array of biocompatible pliable electrically conductive filaments attached hermetically (which complies with FDA requirements regarding hermeticity for implanted medical devices) at their proximal end through an insulating plate or platform and configured for contact with living tissue and electrical communication with such tissue at their distal end. The filament has an inherent pliability by virtue of a helical coil configuration and an excess length preferably perpendicular to the path between the plate and the filament's distal end providing suitable mechanical isolation (strain relief) between the plate and the distal end. Accordingly, the strain relief provides for suitable filament movement in concert with movement of the tissue with which the filament is in contact. In this regard, the pliability of the filament allows the distal end of the filament to remain at the original site of penetration into the selected tissue site despite the movement of the tissue relative to its surrounding environment. Strain relief may be provided by any number of ways including using a coiled filament, such as in the form of a helix, or a filament arranged or bent in an accordion like fashion as well as one or more extended loops that may stretch and retract upon pull and release action. To stabilize and anchor the distal end of the filament in place once positioned, a loop, hook, tines or screw arrangement may be provided or in the alternative a small hole or opening may be provided to for allow tissue in-growth as an anchoring means.

Since the filament is inherently pliable, unless temporarily stiffened, the filament would not be suitable for penetration into relatively dense tissue. Examples of dense tissue include the dura and smooth muscle. To temporarily stiffen the filament, a soluble or dissolvable stiffness enhancing coating is disposed over the filament. Alternately, the filament may be completely encased in a soluble or dissolvable material, figuratively in a fashion as a pencil lead is encased in a wooden pencil. The coating may first be heated prior to application to the filament and then allowed to cool to a stiff hard state. The coating or encasement may be in the form of a biocompatible liquid which dries to a rigid solid state after being applied to or encasing the filament. The coating renders the filament sufficiently rigid such that under appropriate force, the filament is capable of penetrating into dense tissue. Once in place, the stiffness enhancing coating dissolves due to contact with body fluids, the filament, in the absence of such coating, then returns to its initial pliability. Examples of stiffness enhancing coatings and encasements are polysaccharides (sugar and hyaluronic acid), polyesters (polyglycolic acid, polyactic acid and polycaprolactone), polyvinylalcohol, chitin and chitosan and alginates to name a few. Accordingly, the filament may be considered as having a dual state characteristic, a rigid state for penetration into tissue and a pliable state after the filament has penetrated tissue.

Preferably, an electrical insulating layer is disposed over a portion of the filament prior to application of the stiffness enhancing coating to render it non-conductive with tissue in the area adjacent the insulating layer. For a filament with such insulating layer, the stiffness enhancing coating would be disposed over the insulating layer. If desirable, the filament may include anchoring means configured to further anchor the filament in place.

DETAILED DESCRIPTION OF THE PREFERRED EMBODIMENTS

The present disclosure now will be described more fully hereinafter with reference to the accompanying drawings, which form a part hereof, and which show, by way of illustration, specific exemplary embodiments for practicing the invention. This disclosure may, however, be embodied in several different forms and should not be construed as limited to the embodiments set forth herein; rather, these embodiments are provided so that this disclosure will be thorough and complete, and will fully convey the scope to those skilled in the art. Among other things, the present disclosure may be embodied as methods or devices. The following detailed description is, therefore, not to be taken in a limiting sense.

Figure 1:
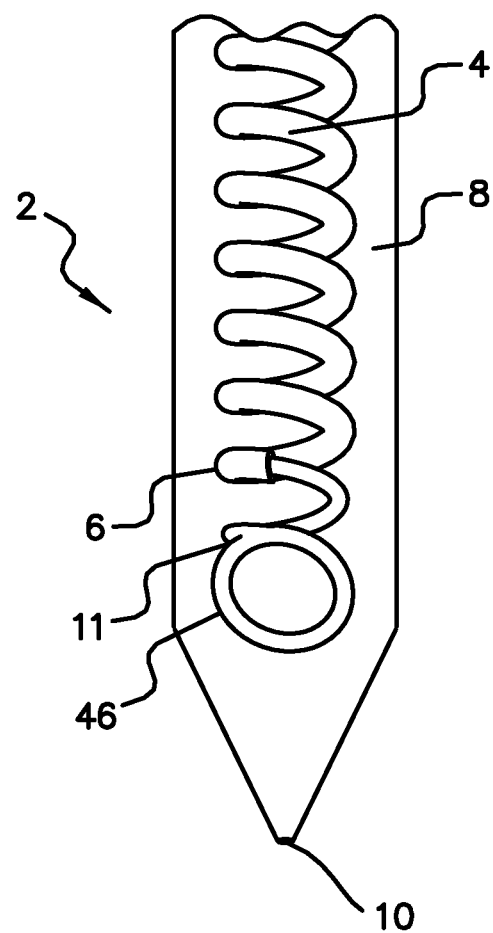
FIG. 1 is a schematic illustration of a filament that includes an electrical insulating layer and a stiffness enhancing coating.

Referring now to FIG. 1, there is shown in detail an example embodiment of an electrode comprising filament 2 of the present invention, configured for use, for example, as electrodes (4) in the package (2) described in U.S. Patent Application Publication U.S. 2007/0067007. Filament 2 is formed of an electrically conductive wire 4 that may be selected from the group that includes platinum, gold, silver, iridium, stainless steal and alloys thereof. Other metals may also be suitable with the proviso that they are biocompatible and do not create an inflammatory reaction with living tissue with which they are in contact. Wire 4 may have a lateral dimension or diameter in the range of about 5 microns to 25 microns and preferably about 6 microns. Wire 4 may have a straight profile, as would be the case for the "bed of nails" as described in U.S. Patent Application Publication U.S. 2007/0067007, but as will discussed in more detail later and as is shown in FIG. 1, wire 4 may be coiled in a helical shape having single or multiple loops or with successive folds, as in an accordion shape, to provide additional strain relief during anticipated significant movement by the patient.

In either dimensional range, filament 2 is configured to be pliable in an uncoated first state and therefore sufficiently flexible and supple enough to bend freely or repeatedly without breaking so as to reliably move in concert with the tissue into which the filament has penetrated without moving away from the original site of penetration as the tissue moves. As will be discussed later, this attribute of the filament is particularly important especially when considering the objective of maintaining the distal tip of filament 2 at its original penetration site independent of tissue movement. The filament 2 is further configured to be stiff and rigid in a coated second state and therefore inflexible and not easily bent to accommodate penetration of the filament into living tissue, such as the dura and the brain. As will be discussed in more detail later, the filament 2 is coated with a dissolvable stiffness enhancing coating which provides the filament with its initial stiffness and rigidity such that subsequent to penetration into tissue by virtue of its stiffness, the coating dissolves and the filament returns to its initial state of being pliable.

Figure 2A:
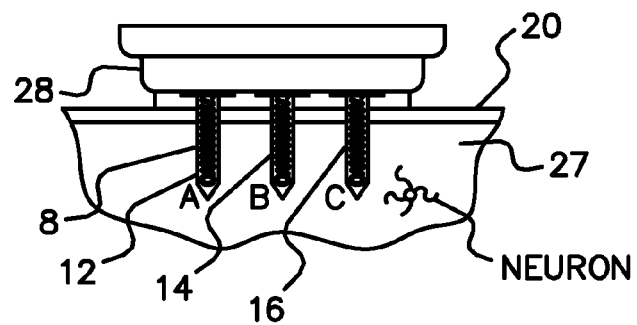
FIG. 2a is a cut-away view of three filaments encased in a stiffness enhancing coating that have penetrated into the dura and brain tissue.
Figure 2B:
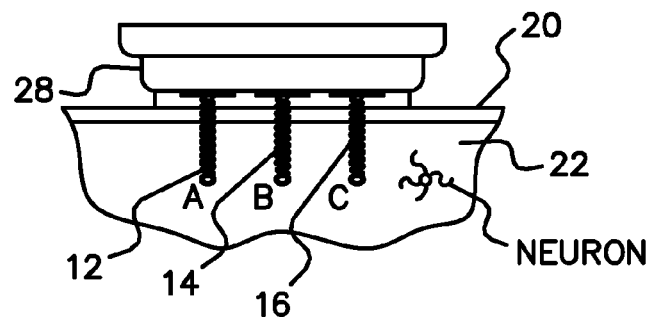
FIG. 2b is a view of the filaments of FIG. 2a after the stiffness enhancing coating has dissolved.
Figure 2C:
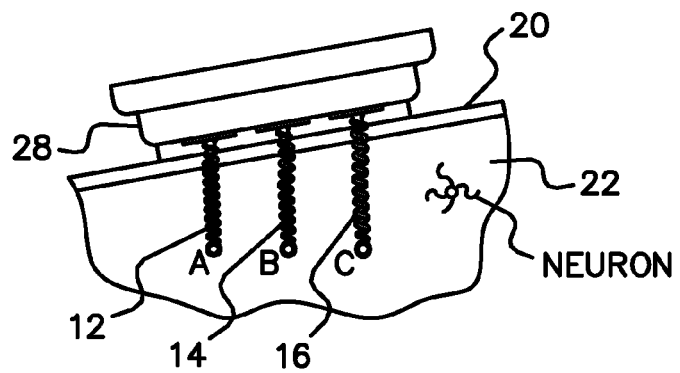
FIG. 2c is a view of the filaments of FIG. 2b wherein the brain tissue has moved relative to the dura.

An illustration of the foregoing is presented in FIGS. 2a, 2b and 2c. Broadly described, electrodes 12, 14 and 16, by virtue of their enhanced stiffness, have penetrated through the dura 20 and into the brain tissue 22. The electrodes 12, 14 and 16, have an initial point of contact with the brain tissue at locations A, B and C respectively. As is shown in FIG. 2a, the electrodes 12, 14 and 16 have an initial straight profile penetrating through the dura 20 and through the brain tissue 22. As is noted, once the stiffness enhancing coating has completely dissolved (FIGS. 2b and 2c), the distal ends of electrodes 12, 14 and 16 are able to move in concert with the corresponding brain tissue at the target locations so as to always maintain monitoring/stimulating the very same brain tissue location as originally selected. As is shown for example in FIG. 2c, as the tissue at location C moves away from the proximal end of electrode 16 (affixed to platform 28), electrode 16 stretches accordingly so as to maintain the distal end of electrode 16 at its original site prior to any tissue movement. Of course, maintaining the distal end of an electrode in place independent of tissue movement ensures that sensory information will be consistently obtained from the target site.

In order to consistently provide for an electrode to consistently follow movements of the brain tissue, the electrode must be very pliable and flexible. As discussed previously however, without adequate stiffness, the electrode would not be very predictable and reliable in being positioned at a target location during the implant procedure at least for penetrating the dura and then brain tissue. To further accommodate maintaining the distal end 11 of the filament 2 at a location in the tissue originally selected, the filament 2 includes a series of coils formed in a helix along its length which are capable of extension and retraction to accommodate an increase and decrease of the longitudinal distance between the proximal and distal ends of the filament respectively. Moreover, both the monitoring and stimulation of tissue preferably should be localized. In order to provide these localized functions the electrode should be electrically insulated along its length except at the regions expected to be in contact with brain tissue. In this manner monitoring and stimulating brain tissue will occur only at the desired brain site.

With reference to FIG. 1, an electrical insulating layer 6 is disposed over the wire 4 substantially along the entire length of the wire 4 except at the distal end 11 which is intended to be in contact with brain tissue. The insulating layer 6 preferably is formed of a biocompatible electrically insulating material such as parylene, polyimide, alumina or zirconia and the like. In the event that electrical contact with tissue is desired at locations other than at the distal end of the wire 4, then the insulating coating may be omitted along the portion of the wire intended to be in electrical contact with brain tissue or any other tissue for that matter.

Again with reference to FIG. 1, wire 4 includes a wire stiffness enhancing coating 8 formed on the surface of the wire. The stiffness enhancing coating is formed over the insulating layer 6 in the region covered by the layer 6 and directly over the wire 4 in the regions not covered by layer 6. The coating 8 is a biodegradable soluble material which when applied to the wire 4 forms a solid rigid encasement for the wire 4. For example, the rigidity or stiffness imparted on wire 4, enables it, to penetrate, under force, through the dura and into brain tissue. Tissue other than the dura and brain tissue is also contemplated for penetration by the filament 2. Nerves and muscles for example, may also be monitored and stimulated with the wire of the present embodiment.

The coating 8 is soluble when in contact with body fluids for example, such as the cerebrospinal fluid. The coating 8 may be applied in varying thicknesses to control the rate of dissolution after implant and to either increase or decrease the wire stiffness as desired. The applied thickness of the coating 8 also impacts the length of time for complete dissolution of the coating. Once the coating is completely dissolved however, the wire 4 returns to its original uncoated flexibility and pliability and is therefore adapted to move in concert with movement of the tissue in which it has penetrated without departure from the original site of penetration. It should be noted that although FIG. 1 shows the coating 8 disposed over insulating layer 6 which extends over a substantial length of the wire 4, the coating 8 may be disposed over a wire 4 completely lacking the insulating layer 6. An example of a material suitable for insulating layer 6 is paralene, however other materials known in the art are also suitable as insulating materials.

To facilitate initial penetration into the dura and brain tissue, the tip 10 of the coated wire 4 may be shaped into a sharp conical profile. As before, once implanted, and the coating completely dissolved; only the distal end 11 of the filament 2 remains in electrical contact with living tissue. Materials contemplated for stiffness enhancing coatings include but are not limited to polysaccharides, polyesters, polyvinyl alcohol, chitin, chitosan and alginates.

Application of the stiffness enhancing coating 8 to a filament may be accomplished either to individual filaments prior to assembly in an electrode package (2) such as described in U. S. Patent Application Publication 2007/0067007 or when the filaments are assembled in an electrode package and then coated with the stiffness enhancing coating 8.

The wire 4 may be immersed in a selected coating 8 when the coating is in liquid form and then removed after a drying cycle. Typically a canister or mold into which a liquid coating 8 may be poured may be dimensioned laterally to receive a filament without making contact with the filament and provide thereby a coating of a desired dimension. Once the coating 8 dries to a hardened state, the coated filament or encased filament, as the case may be, may be extracted from the canister in anticipation of use. The bottom portion of the canister may be shaped in a sharpened conical profile to impart thereby, a sharpened distal end of the filament 2. The canister preferably has a contoured or conical profile to provide for easy withdrawal of the filament from the canister. Other techniques known in the art may also be used to sharpen the distal end 11 of the filament 2. Furthermore, the coating 8 may also include an anti-inflammatory drug as a pre-caution against inflammation during and after the insertion of the filament in tissue.

Figure 3A:
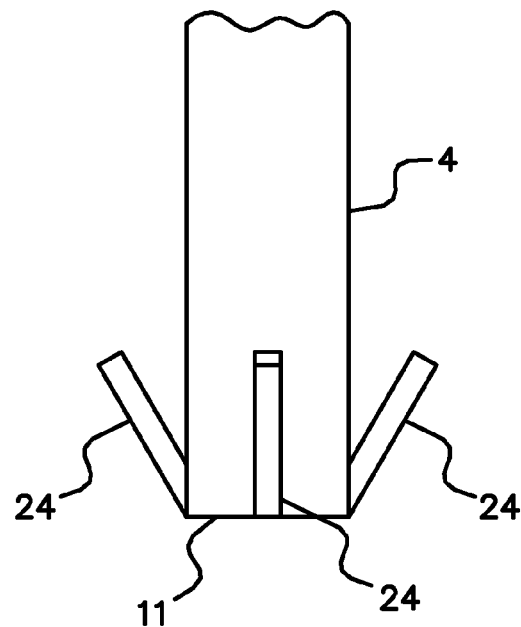
FIGS. 3a and 3b illustrated examples of alternate filament anchoring techniques.
Figure 3B:
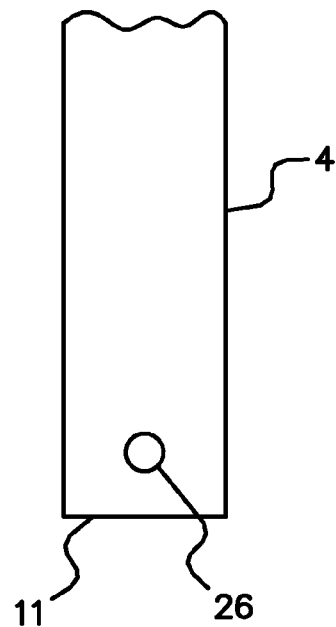

Referring now to FIG. 1 and FIGS. 3a and 3b, there are shown techniques for anchoring the wire 4 in place once the wire 4 has penetrated into the desired tissue. As shown in FIG. 1, an anchoring loop (46) positioned at the distal end 11 of wire 4 provides for tissue ingrowth and attachment to tissue at the target site. Once tissue has encircled around and through the loop at the distal end 11, the electrode will be essentially anchored in place. Other examples of locking and anchoring techniques are shown in FIG. 3a for example, where tines 24 extend from the distal end 11 of wire 4 and are of sufficient length to be entrapped by the tissue with which they are in contact. In this manner the wire 4 may be further locked in position in the selected tissue site. An alternate embodiment of anchoring the wire 4 in place is shown in FIG. 3b. An orifice 26 is positioned at the distal end 11 of wire 4 and provides for tissue ingrowth therethrough. As tissue extends through orifice 26 and connects with surrounding tissue, wire 4 will thereby be anchored in place.

Figure 4:
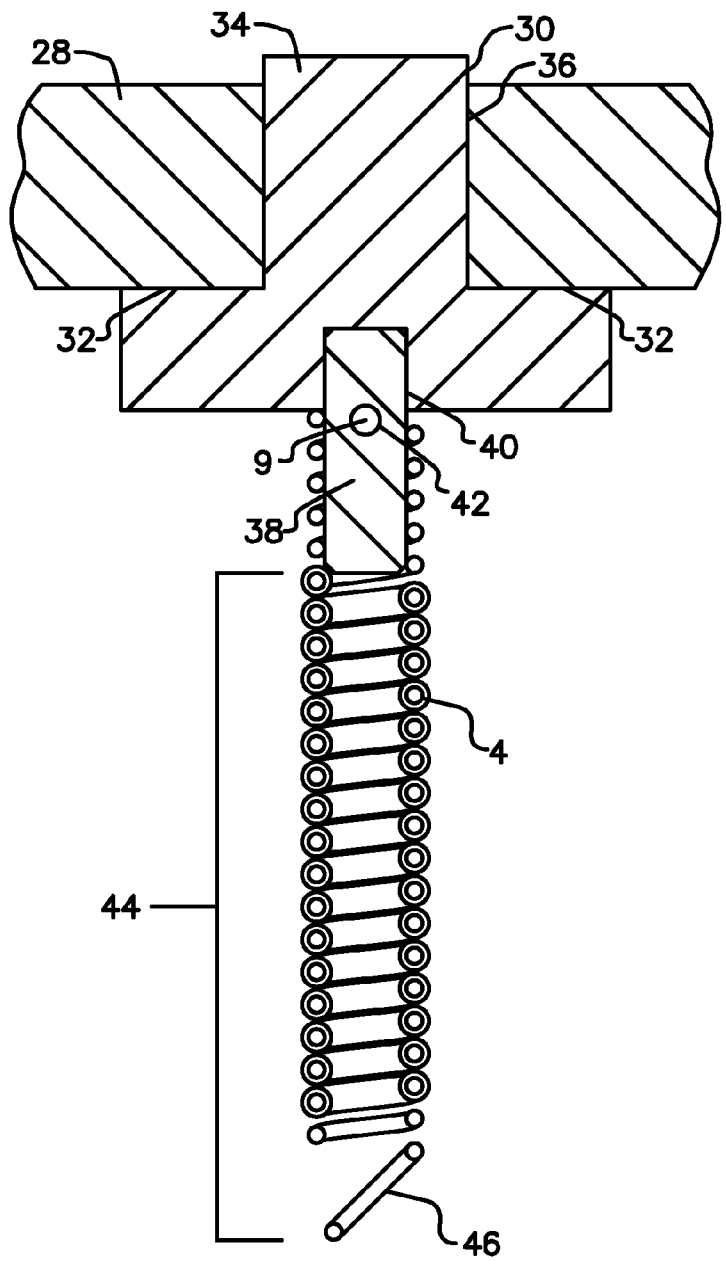
FIG. 4 is a simplified drawing illustrating attachment of a filament to a feedthrough assembly.

An example mounting for the wire 4 is shown in FIG. 4. A ceramic platform or receptacle 28 for a single or multiple filaments, as the case may be, includes a feedthrough assembly 30. The platform 28 may be formed of an electrically non-conductive ceramic such as zirconia and the feedthrough assembly 30 may be formed of an electrically conductive metal such as TI-64. A feedthrough stem portion 34 extends through the platform 28 through a corresponding opening 36 in the platform 28 which provides a communication path for electrical signals between wire 4 and signal processing electronics (not shown) coupled to the stem portion 34. Attachment of the feedthrough assembly 30 to the platform 28 may be by way of brazing whereby a Nickel braze material is placed between the platform 28 and the feedthrough assembly 30 along the mutual area of contact 32. Once the feedthrough assembly 30 is positioned in the platform 28, a brazing process is undertaken to anchor such parts together.

A filament pin 38, preferably formed of Iridium, is press fit into a corresponding feedthrough opening 40 provided in feedthrough assembly 30. Alternately, the pin 38 may be brazed to the feedthrough assembly 30 so as to anchor the pin in place. The pin 38 includes a small passageway 42 sized to receive the proximal end 9 of wire 4 and after the wire 4 is inserted in the passageway it may be secured in place by conventional welding techniques. Preferably, the radius of the spiral coils of wire 4 shown in FIG. 4, is in the range of about five times the thickness of the wire, so that for a wire having a thickness of about 6 microns, the radius of the spiral coil is about 30 microns. The number of coils and the length of the spiral away from pin 38 may be selected based upon anticipated movement of the patient. Accordingly, the greater the expected movement of the patient, then the corresponding number of coils and the overall length 44 of the spiral, may be determined.

Once the assembly shown in FIG. 4 is completed, the assembly is coated with a layer of an electrical insulating material such as paralene. The thickness of the paralene layer preferably, may be in the range of from one to two microns. Other similar materials known in the art, may also be used. Prior to application of the insulation layer however, provision should be made to exclude a portion of the filament from exposure to the insulation layer, where electrical contact with tissue is desired. For example, the anchoring loop 46 is temporarily covered just prior to application of the insulation layer to ensure that the anchoring loop 46 remains free of insulation so it will make proper electrical contact with tissue. The insulation layer ensures that adjacent coils will not short circuit and thus provide false positives or stimulate unintended tissue, in the event that the patient moves to an extent that adjacent coils come in contact with each other.

Figure 5:
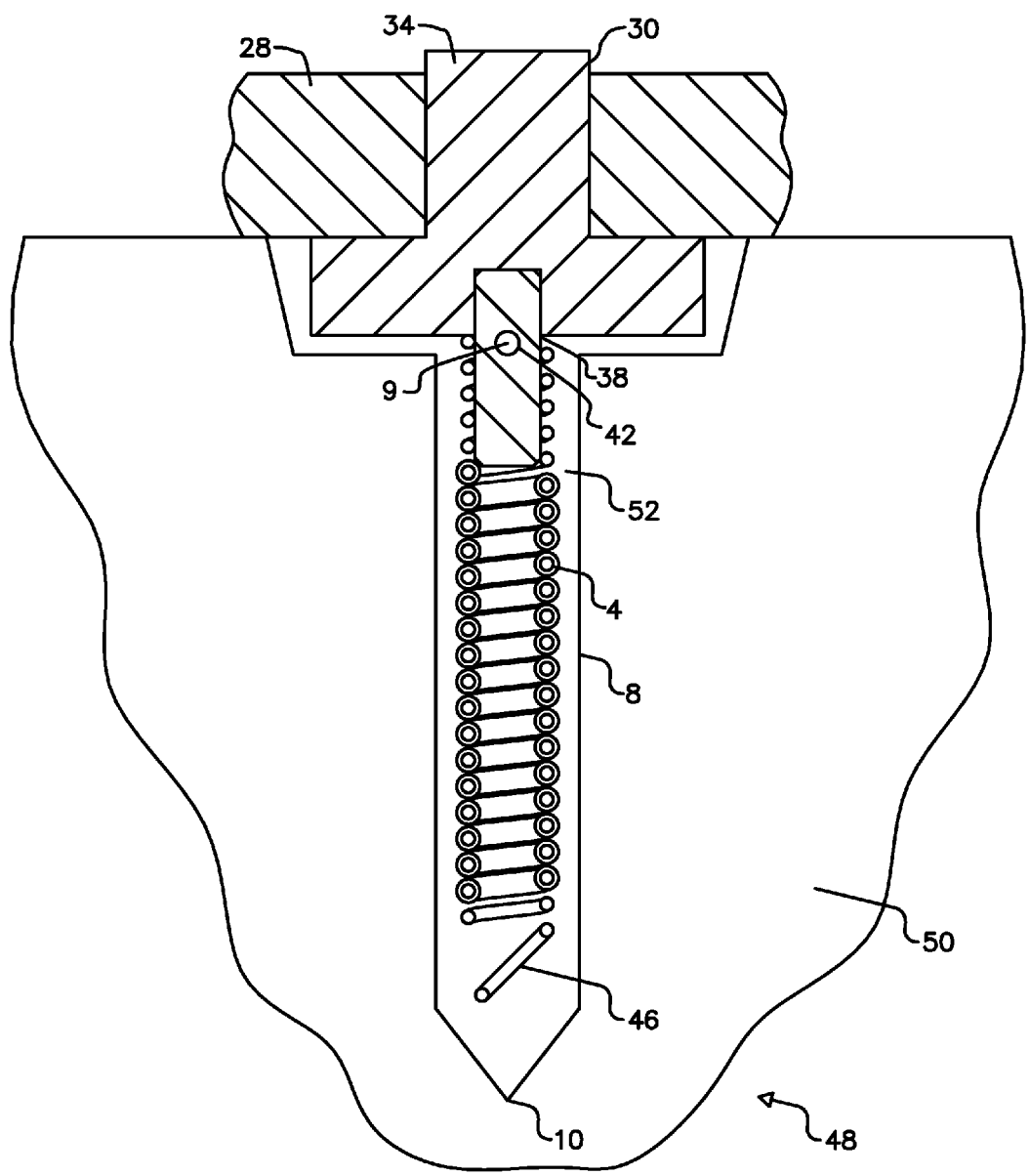
FIG. 5 is a simplified drawing illustrating insertion of a filament in a mold to receive a stiffness enhancing material.

Referring now to FIG. 5, there is shown a schematic representation of a wire 4 positioned in a mold 48 during application of stiffness enhancing coating 8. The mold 48 preferably comprises a Teflon (or the like) block 50 having a contoured opening 52 of sufficient dimension to receive wire 4 (having a paralene coating), pin 38 and the bottom portion of feedthrough assembly 30. The sides of the opening 52 are contoured, and in the case of the example shown, a conical shape, to provide easy extraction of the assembly 30 from block 50 once the stiffness enhancing coating solidifies. The opening 52 may be machined into the Teflon block 50 using known machining techniques. Prior to insertion of assembly 30 into opening 52, a stiffness enhancing material in liquid form preferably but not necessarily preheated, is poured into opening 52. While the material is in the heated state, the assembly 30, and in the case of an array of assemblies 30, are lowered into a respective opening 52. The assemblies are held in place as the material cools to a rigid and hardened state, whereupon the assemblies are then extracted from the block 50 with the wire 4 encased/coated in a rigid mold and form thereby in this case coating 8. Although FIG. 1 illustrates a straight parallel coating 8, it is to be understood that alternate shapes as shown in FIG. 5 are contemplated by the invention as a function of the coating process used.

Figure 6:
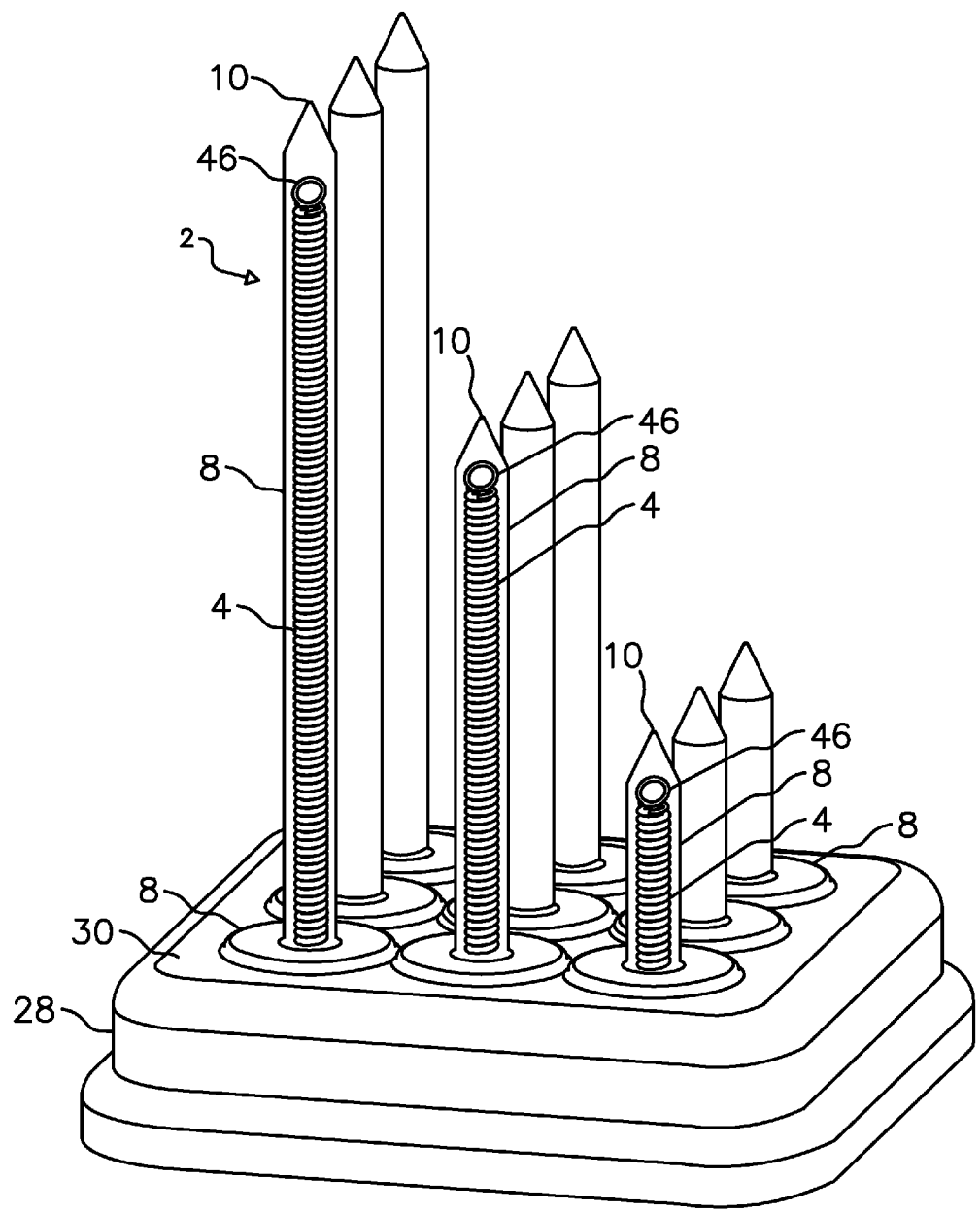
FIG. 6 is an illustration of an example array of filaments subsequent to application of the stiffness enhancing coating.

Referring now to FIG. 6, there is illustrated an array of filaments subsequent to the application of the stiffness enhancing coating 8. As can be noted, the wire 4 and the feedthrough assembly 30 are encased in coating 8. Obviously, the number of encased wire(s) 4 shown in FIG. 6 depends upon the application contemplated. Various lengths of the wires are also depicted to illustrate design options contemplated by the invention.

Figure 7:
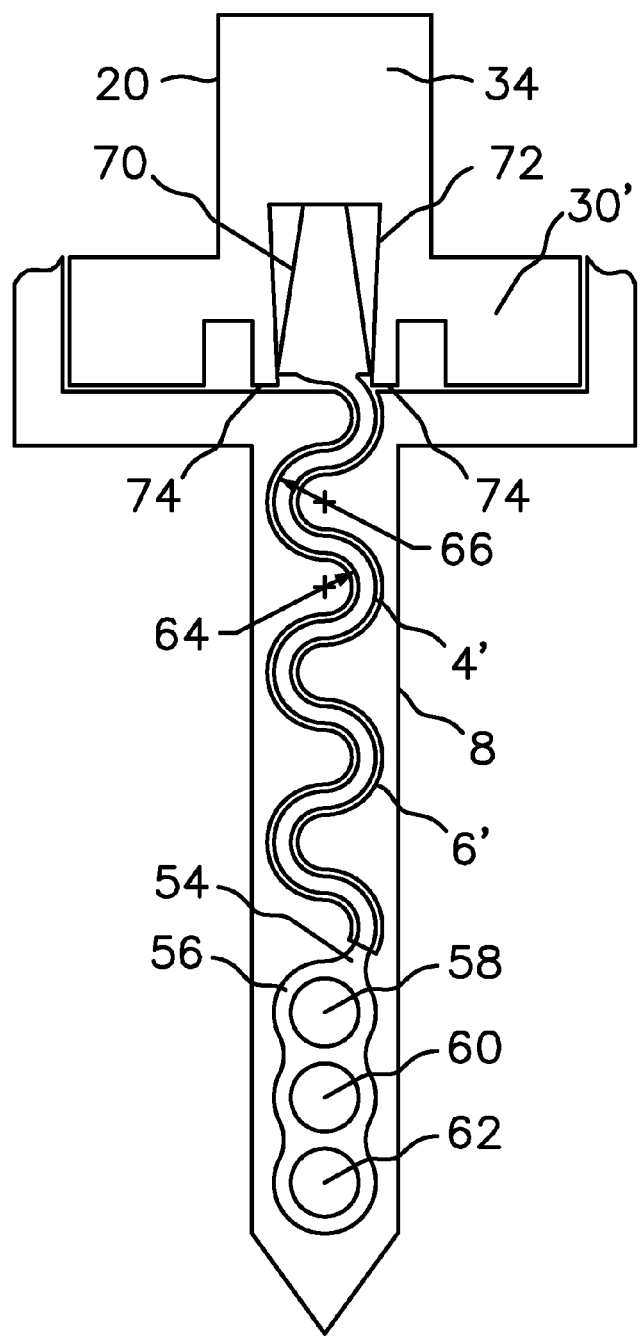
FIG. 7 is a front cut-away view of an alternate embodiment of the filament of FIG. 1.

Referring now to FIG. 7, there is shown an alternate embodiment of a stiffness enhanced wire 4' mounted in a feedthrough assembly 30'. Wire 4' includes an electrical insulating layer 6' and at the wire's distal end anchor eyelets 56. As shown in FIG. 7, anchor eyelets 56 comprise individual eyelets 58, 60 and 62 and it is to be understood that any number of eyelets are contemplated by the invention depending upon application. The eyelets 58, 60 and 62 are generally circular in form due to ease of manufacture and provide means for tissue ingrowth once the distal end 54 of wire 4' is positioned at the desired site in tissue. Once tissue ingrowth through and around the eyelets is substantial, the eyelets maintain the distal end 54 anchored in place. As previously described, alternate anchoring techniques, such as tines, fish hook barbs and the like may also be used as anchoring techniques.

As shown in FIG. 7, wire 4' preferably is in the shape of a series of pliable consecutive "S" shaped curves along the length of the wire 4'. The inside radius 64 and outside radius 66 of the "S" shaped curves may be selected based upon application. The inside radius 64 preferably is about 20 microns and the outside radius 66 preferably is about 30 microns. If pulled to a straight profile, the wire 4' may be stretched to 50% or greater in length relative than being in a curved condition. The ability to stretch ensures that once the wire 4' is anchored in place at the distal end, the feedthrough assembly may move in various directions while the distal end 54 remains anchored in place at the desired tissue site.

Figure 8:
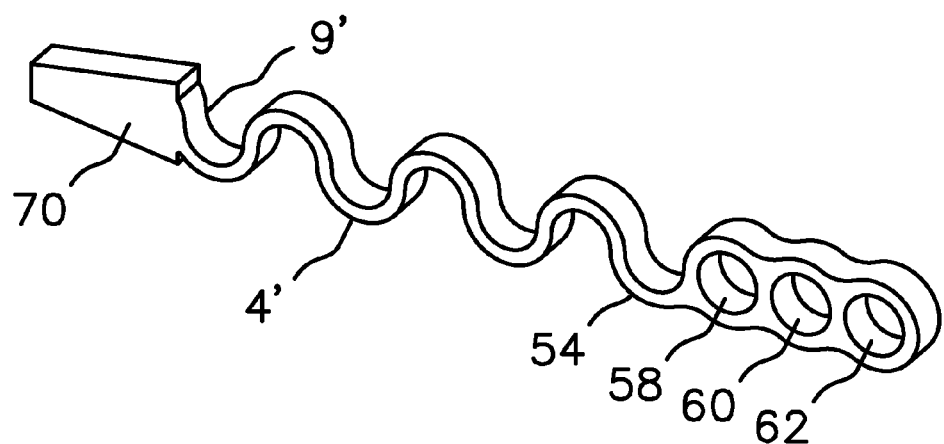
FIG. 8 is a perspective view of the filament of FIG. 7.

The wire 4' may be formed from a thin foil having a thickness preferably about 10 microns and having a width preferably about 25 microns. Appropriate materials for the wire 4' are iridium; an alloy of 80% Platinum and 20% Iridium; and an alloy of 90% Platinum and 10% Rhodium. As shown in FIG. 8, the proximal end 9' of wire 4' terminates in a tapered extension 70. A cavity 72 positioned essentially centrally in feedthrough assembly 30' is sized to receive extension in a quasi-press fit manner. Bendable crimp lugs 74 depend from the edge of cavity 72 such that once the extension 70 is positioned in cavity 72, squeezing or crimping lugs 74 against extension 70 causes the extension 70 to abut against the inner surface of cavity 72, thereby locking the extension 70 in place. Other methods of locking extension 70 in place known in the art are also contemplated by the invention.

By virtue of the locking crimp, a reliable and continual electrical connection is maintained between wire 4' and feedthrough assembly 30'. As noted in FIG. 7, an electrical insulation layer 6' is disposed over wire 4' in a manner as previously described. Furthermore, a stiffness enhancing material 8 is also provided such that the wire 4' is embedded in the material as previously described. Depending upon the application, the stiffness enhancing material may also contain: an anti-fibrotic agent such as Halafuginone to prevent or reduce connective tissue growth; a neural growth hormone to cause neurons to grow and migrate towards the anchor eyelets 58, 60 and 62 or tines 24 as the case may be; anti-inflammatory agents such as Methylprednisolone, Dexamethasone and Triamcinolone; and anti-infection agents.

Figure 9:
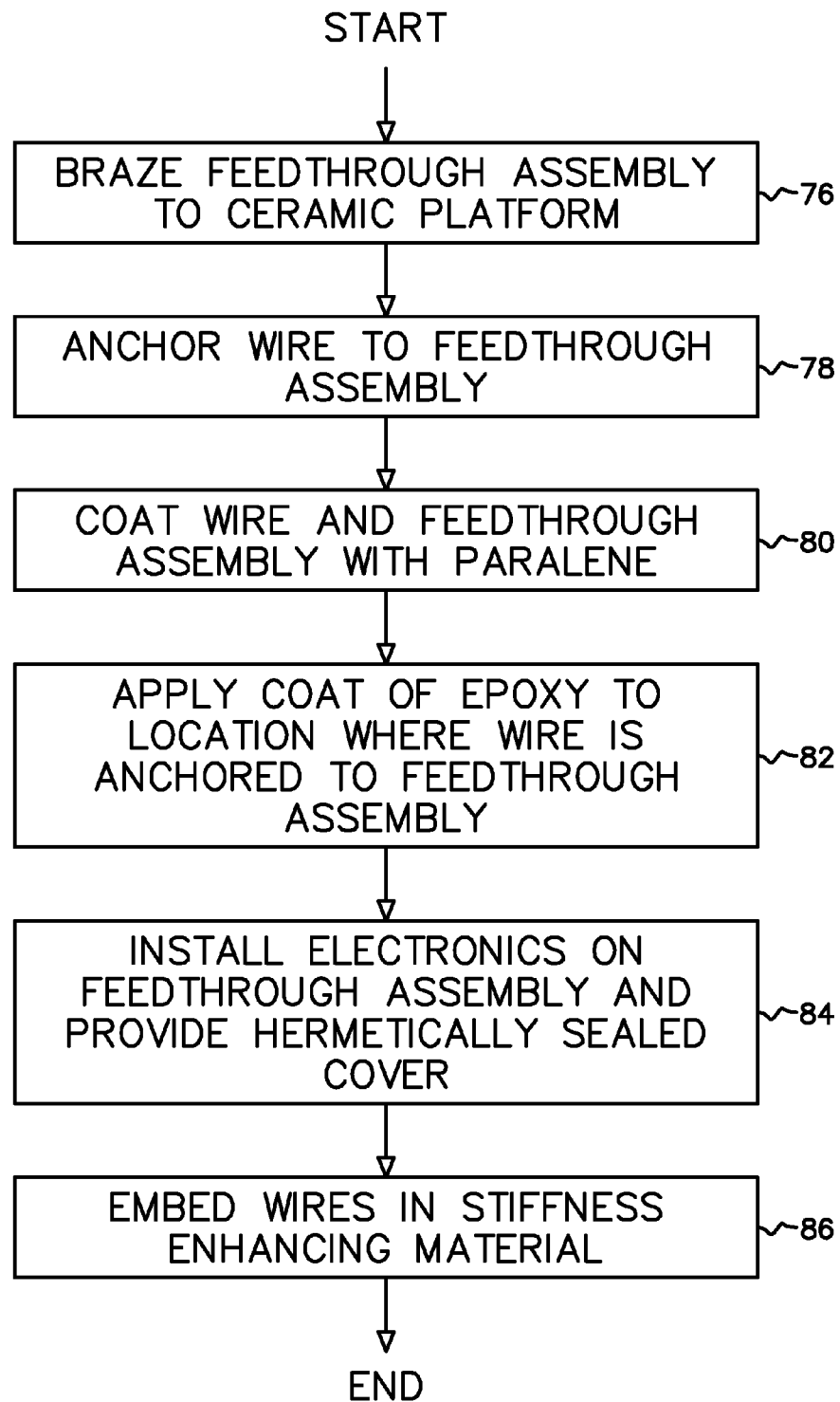
FIG. 9 is a flow chart of the method of assembly of the filament of FIG. 7.

In accordance with the invention, in assembling an array of electrodes, otherwise known in the art as a "bed of nails" (BON), a number of manufacturing steps are undertaken. Referring now to FIG. 9, initially at step 76, feedthrough assembly (30 or 30' as the case may be) is brazed to ceramic platform 28 typically using a furnace brazing process with filler materials appropriate for brazing titanium alloys for example to a ceramic such as zirconia. Next at step 78, the wire 4 or 4' may be fitted into (as shown in FIG. 5) and then welded in pin 38 or crimped in place as is shown in FIG. 7. Next at step 80, the wires and exposed portion of the feedback assemblies are coated with a thin layer of electrical insulating material such as paralene to provide electrical insulation between adjacent wires. Next at step 82, a thin layer of epoxy is applied in the region of where the wires are secured to the feedthrough assemblies. The epoxy prevents the insertion force of the BON into tissue from breaking the electrical insulation covering the wires. Next at step 84, a hermetic cover is welded over the feedthrough assembly once processing electronics are located on and coupled to the see-through. Next in step 86 of the BON assembly process, the wires are embedded or cast into the stiffness enhancing material as previously described.

Although the invention has been described and illustrated in detail, it is to be clearly understood that the same is by way of illustration and example only and is not to be taken by way of limitation, the spirit and scope of this invention being limited only by the terms of the appended claims.

What is claimed is:

1. A method of providing a stiffness enhancing material to a pliable filament having a distal tip comprising the steps of:
   providing a mold having a contoured opening dimensioned such that the distal tip with a length of the filament can extend into the contoured opening without contact with the mold;
   filling the contoured opening with a stiffness enhancing material, said material having an initial liquid state;
   immersing the filament into the stiffness enhancing material;
   maintaining the filament in the mold until the stiffness enhancing material achieves a solid state; and
   withdrawing the filament from the mold once the material achieves the solid state, whereby said filament is thereby encased in a stiffness enhancing material, wherein the filament is an electrically conductive wire.

2. The method of claim 1, further comprising the step of heating the stiffness enhancing material prior to immersing the filament therein.

3. The method of claim 1, further comprising the step of selecting the stiffness enhancing material from the group consisting of polysaccharides, polyesters, polyvinyl alcohol, chitin, chitosan and alginates.

4. The method of claim 1, further comprising the step of providing an anti-inflammatory drug to the filament.

5. The method of claim 1, further comprising the step of providing the contoured opening in a conical shape for facilitating the withdrawing of the filament from the mold.

6. The method of claim 1, wherein a bottom portion of the contoured opening has a sharpened conical profile.

7. The method of claim 1, wherein the filament comprises an anchor.

8. The method of claim 7, wherein the anchor is selected from the group consisting of a loop, a hook, and one or more proximal-facing tines.

9. The method of claim 1, wherein the stiffness enhancing material is biodegradable.

10. The method of claim 1, wherein the contoured opening is dimensioned such that the stiffness enhancing material completely encases the filament when the filament is withdrawn from the mold.

11. A method of providing a stiffness enhancing material to a pliable filament comprising the steps of:

providing an anti-inflammatory drug to the filament;

providing a mold having a contoured opening dimensioned to receive the filament along its length without contact with the filament;

filling the contoured opening with a stiffness enhancing material, said material having an initial liquid state;

immersing the filament into the stiffness enhancing material;

maintaining the filament in the mold until the stiffness enhancing material achieves a solid state; and withdrawing the filament from the mold once the material achieves the solid state, whereby said filament is thereby encased in a stiffness enhancing material.

12. The method of claim 11, further comprising the step of heating the stiffness enhancing material prior to immersing the filament therein.

13. The method of claim 11, further comprising the step of selecting the stiffness enhancing material from the group consisting of polysaccharides, polyesters, polyvinyl alcohol, chitin, chitosan and alginates.

14. The method of claim 11, further comprising the step of providing the contoured opening in a conical shape for facilitating the withdrawing of the filament from the mold.

15. The method of claim 11, wherein a bottom portion of the contoured opening has a sharpened conical profile.

16. The method of claim 11, wherein the filament is an electrically conductive wire.

17. The method of claim 11, wherein the filament comprises an anchor.

18. The method of claim 17, wherein the anchor is selected from the group consisting of a loop, a hook, and one or more proximal-facing tines.

19. The method of claim 11, wherein the stiffness enhancing material is biodegradable.

20. The method of claim 11, wherein the contoured opening is dimensioned such that the stiffness enhancing material completely encases the filament when the filament is withdrawn from the mold.

* * * * *